United States Patent
Rossa et al.

(10) Patent No.: US 7,176,341 B2
(45) Date of Patent: Feb. 13, 2007

(54) METHOD AND DEVICES FOR PRODUCING NAPHTHALENE FROM COKE PRODUCED FROM COKE OVEN CRUDE GAS

(75) Inventors: Frank Rossa, Bochum (DE); Hans-Josef Giertz, Ratingen (DE); Horst Schröder, Dortmund (DE)

(73) Assignee: Deutsche Montan Technologie GmbH, Essen (DE)

(*) Notice: Subject to any disclaimer, the term of this patent is extended or adjusted under 35 U.S.C. 154(b) by 609 days.

(21) Appl. No.: 10/398,501

(22) PCT Filed: Oct. 2, 2001

(86) PCT No.: PCT/EP01/11361

§ 371 (c)(1), (2), (4) Date: Apr. 3, 2003

(87) PCT Pub. No.: WO02/32840

PCT Pub. Date: Apr. 25, 2002

(65) Prior Publication Data

US 2004/0059175 A1    Mar. 25, 2004

(30) Foreign Application Priority Data

Oct. 17, 2000  (DE) ................ 100 51 349

(51) Int. Cl.
*C10B 51/00* (2006.01)
*C07C 7/00* (2006.01)

(52) U.S. Cl. .......... 585/800; 585/833; 201/29; 201/30; 202/91; 208/33; 95/189; 95/205; 55/48; 55/49; 55/53; 55/85; 55/89

(58) Field of Classification Search .......... 55/48, 55/49, 53, 85, 89; 95/189, 205; 201/29, 201/30; 202/91; 208/33; 585/800, 833
See application file for complete search history.

(56) References Cited

U.S. PATENT DOCUMENTS

| | | | | |
|---|---|---|---|---|
| 2,956,639 A | * | 10/1960 | Stirling et al. | 95/205 |
| 4,234,389 A | * | 11/1980 | Lynn et al. | 201/30 |
| 4,286,971 A | * | 9/1981 | Burcaw et al. | 95/189 |
| 4,441,987 A | * | 4/1984 | Broadhurst | 208/33 |

FOREIGN PATENT DOCUMENTS

DE    4012146 A1  * 10/1991

* cited by examiner

*Primary Examiner*—Gienn Caldarola
*Assistant Examiner*—Prem C. Singh
(74) *Attorney, Agent, or Firm*—Andrew Wilford

(57) ABSTRACT

A method and apparatus are disclosed for recovering pure naphthalene from hot crude coke oven gas. The hot crude coke oven gas is directly cooled by means of sprinkling water directly thereon, and the naphthalene is recovered by subsequent filtering out of tar and other impurities, followed by cooling to obtain crystalline pure naphthalene. More specifically, after direct cooling of the hot crude coke oven gas, the gas is then guided through an electrofilter to be subsequently cooled in such a manner that the naphthalene contained in the crude coke oven gas is separated from the gaseous phase and is obtained in the form of pure naphthalene crystals without any required additional treatment.

19 Claims, 3 Drawing Sheets

METHOD AND DEVICES FOR PRODUCING NAPHTHALENE FROM COKE PRODUCED FROM COKE OVEN CRUDE GAS

FIELD OF THE INVENTION

The invention relates to a method of recovering naphthalene from coke oven crude gas as well as apparatus suitable for that purpose.

BACKGROUND OF THE INVENTION

In the thermal treatment of coal under the exclusion of air in a coke oven, coke oven crude gas is produced which is cooled by means of water droplets [trickling water] in a crude gas condenser to about 80° C. and is saturated with water vapor. As a result, about 20% of the naphthalene entrained with the coke oven crude gas is bound up in tar in the liquid phase. The remaining 80% of the naphthalene is then condensed in an indirect crude gascooling together with tarry aqueous components in a precooler. This condensate is initially fed to the crude gas condenser, there heated to about 80° C. and supplied to a tar separation in which the separation of crude tar from cooled water is effected. The naphthalene contained in the crude tar is recovered from the crude tar in highly expensive processes from a process technology view point. Initially in a distillation of the tar a naphthalinol is produced is then subjected to crystallization in which the crude naphthalene is deposited out to recover pure naphthalene, further processes like chemical reactions, (for example with sodium hydroxide and sulfuric acid) are required or the raw naphthalene is distilled again.

OBJECT OF THE INVENTION

The invention has as its object to provide a method of recovery of naphthalene from coke oven crude gas as well as to provide an appropriate apparatus by which the naphthalene can be recovered in high purity at low cost in a simple manner and way.

SUMMARY OF THE INVENTION

According to the invention, the crude gas coming from the coke oven is cooled as is customary with the aid of sprinkling water thereon in the crude gas condenser directly to about 80° C. This results in a liquid phase and a gas phase. The liquid phase is fed to tar separation in which the separation into tar and coal water is effected. A part of the coal water is again used for the direct crude gas cooling as the trickling water. The gaseous phase is fed through an electrostatic filter in which the solids content and tar content of the coke oven crude gas is reduced at a temperature of about 80° C. by 99.99%.

Since the deposition in the electrostatic filter is carried out at a temperature of about 80° C., the naphthalene (predominantly in the gaseous form) remains in the coke oven crude gas after passing the electrostatic filter. The coke oven crude gas is then cooled from about 80° C. to about 20° C. such that the naphthalene contained in the crude gas deposits out. Since the solids as well as the tar have already been deposited in the electrostatic filter, the naphthalene here is a very pure naphthalene which is a saleable product which can be delivered directly to the consumer.

So that the naphthalene in the electrostatic filter will not separate out, the electrostatic filter is isolated or even heated so that the isothermal requirements for the electrostatic filter will be maintained at about 80° C. The tar which has been separated out [in the electrostatic filter] according to the invention serves to protect the inner surfaces of the electrostatic filter from corrosion, the electrostatic filter can be composed of simple structural steel (for example: ST 37-3).

The tar deposited in the electrostatic filter is especially low in naphthalene since, as has been observed above, the naphthalene remains in the coke oven gas. This low naphthalene tar is supplied to a tar separation stage. Based upon the low naphthalene content (about 2% residual naphthalene content), emulsion formation in the tar-water separation is reduced and the tar separation improved. In addition, the residence time required for the tar-water separation is also reduced. The tar water separation can also be carried out at a somewhat lower temperature since the emulsion formation is reduced.

According to a variant of the process, it is also possible to feed the low naphthalene tar from the electrostatic filter, since it is close to water free, not to the tar separation stage but directly to the tar storage receptacle. This relieves load on the tar separation stage. The low naphthalene tar can also be stored in a separate tar storage receptacle and used for other processes like, for example, precooler flushing.

The naphthalene can be recovered from the crude gas downstream of the electrostatic filter by direct or indirect cooling.

In the direct cooling, the coke oven crude gas is directly cooled with water downstream of the electrostatic filter. The naphthalene is thereby separated out and is then separated from the water. Since the water is approximately free from impurities, it can be fed in a circulation with corresponding recooling. The recooling of the circulated water can be effected directly or indirectly. The excess water is supplied to the condenser.

With indirect cooling the naphthalene crystallizes on the cooling surfaces.

The naphthalene which is crystallized out can be recovered by different techniques and in various ways: One possibility is to recover the naphthalene by heating. The heating can be effected directly or indirectly. The cooling surfaces can be heated by a heating medium, both on the "naphthalene side" and also upon the other side and the naphthalene thus removed and transported through heated conduits to the shipment point.

The heating can be effected also by heating rods which can be built into the apparatus at appropriate locations.

Another possibility is to flush the naphthalene with previously heated liquid naphthalene. Liquid naphthalene can also be used for the indirect heating.

It is also possible to dissolve the crystallized-out naphthalene with a solvent from the cooling surfaces and then to recover it from the solvent.

The recovery of the crystallized-out naphthalene can also be effected mechanically, for example, with the aid of a shaver. Either the shaver or the cooling surface is moved to recover the naphthalene.

It is also possible to recover the crystallized-out naphthalene with the aid of mechanical vibrations which can be produced by an impactor or shaker or with the aid of an imbalanced motor.

In the aforedescribed method the recovery of naphthalene is carried out discontinuously, that is in a first method step the naphthalene is crystallized out and in a second method step the crystallized-out naphthalene is recovered.

It is however also possible to carry out the recovery of naphthalene continuously or quasicontinuously. In this mode of operation, a device is fed segment wise into the cooling region or into the naphthalene recovery region. A continuous operation is also possible with the use of a shaver or vibration generator.

For carrying out the method of the invention, it is only necessary to have an electrostatic filter and a device appropriate for the deposition of naphthalene from which the deposited can be recovered.

For an after-fitting of existing coking plants it is possible to provide only the electrostatic filter and use the previously provided precooler.

If the electrostatic filter is provided downstream from the precooler, the electrostatic filter can be built into the crude gas path upstream of the precooler.

This electrostatic filter can be built into the crude gas path ahead of the precooler. Electrostatic filters following the precooling are superfluous in the method according to the invention.

Since existing coke plants as a rule have multiple precoolers, the method can be carried out as follows with the precoolers which have previously been provided:

One group of for example two precoolers is used to crystallize out the naphthalene. The remaining precoolers run in the usual precooler operation with tar flushing. In a quasi continuous operation, for example, one precooler is used to crystallize out the naphthalene and one precooler is used for the naphthalene recovery. With an increase in the pressure loss in the precooler for naphthalene recovery or with an increase in the crude gas discharge temperature by a maximum of 2° C., the crude gas is no longer fed through this precooler but through the [other] precooler which is in standby status following the naphthalene recovery.

The naphthalene crystallized out on the cooler tubing is recovered by heating the tubing up. The cooler tubing can be heated from the interior or from the exterior. A combination of internal and external heating is however also possible. After the naphthalene has been recovered from the precooler, it is switched over and the precooler can again be used for crystallizing out of the naphthalene while the naphthalene is recovered from the other precooler.

In this mode of operation, a reduced naphthalene recovery can be carried out and a switchover to partial or also complete cooler operation in the classical manner.

In this mode of precooler operation it is advantageous to prevent the naphthalene from plugging up the precooler by flushing the precooler with the low naphthalene tar from the electrostatic filter.

With the method according to the invention of recovering naphthalene from coke oven crude gas, the apparatus suitable for recovering naphthalene can use a conventional precooler. In the cooling step, the naphthalene crystallizes out on the cooling tubing from the gas phase and then the naphthalene is recovered in accordance with the above described process. During the naphthalene recovery the coke oven crude gas is led through the precooler which is in a stand by state.

The precooler can be equipped for a quasicontinuous naphthalene recovery. Then the precooler must be equipped segment wise with controllable valves. In this manner and way it is possible to carry out simultaneously in the precooler a cooling operation for crystallizing out the naphthalene and a naphthalene recovery operation with heating up of the naphthalene.

For the recovery of the naphthalene, another apparatus is also possible. It is only necessary that a cooling surface be provided from, which using the above described process, the naphthalene can be recovered. As cooling surfaces for example, a drum or disk can be used. If this drum or these disks are equipped with a shaver, the naphthalene recovery can also be effected continuously.

It is also possible to crystallize out the naphthalene in a tube cooler whose tubes are cooled at their outer walls. The naphthalene then deposits on the tubing inner walls and can be recovered with the described method.

The aforedescribed and claimed components and those used as described in the examples according to the invention can be selected as to their dimensions, their shapes, their choice of materials and their technological conceptions, without special preconditions so that they can be employed without limitations in the full range of applications.

BRIEF DESCRIPTION OF THE DRAWINGS

Further details, features and advantages of the subject of the invention are given in the dependent claims and in the following description relevant to the accompanying drawing in which preferred embodiments of the method of the invention are given by way of example and are illustrated.

The drawing shows.

DETAILED DESCRIPTION OF THE DRAWINGS

Figure 1:
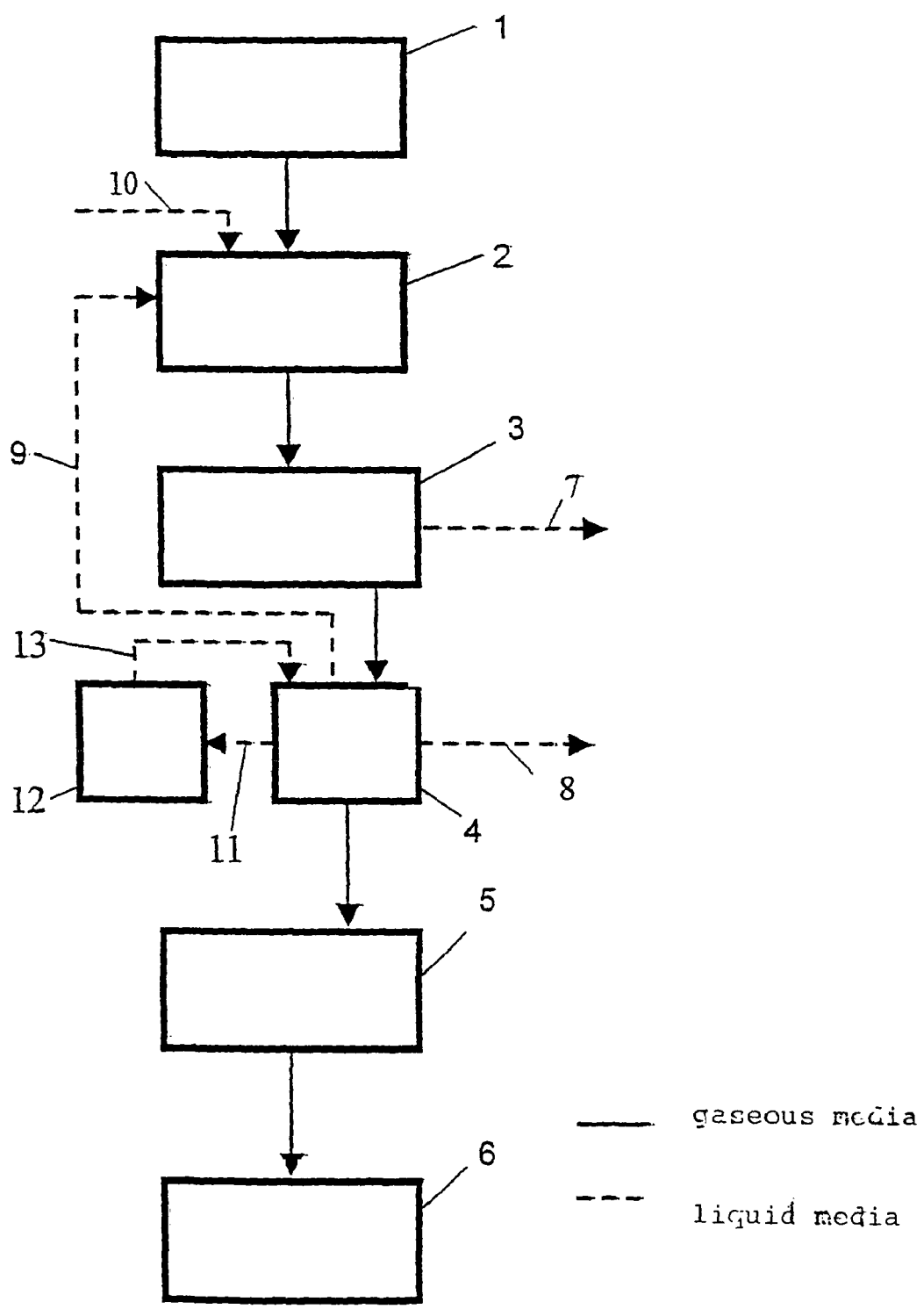
FIG. 1 is a schematic illustration of the method for recovering naphthalene from coke oven crude gas with direct cooling.

From FIG. 1 it is seen that a crude gas coming from the coke oven 1 is cooled in a crude gas condenser 2 with water droplets supplied by a line 10 from a temperature of about 800° C. to about 80° C. The coke oven crude gas is fed through an electrostatic filter 3 in which the solids and tar content of the coke oven crude gas is reduced by 99.99%. The precipitated tar is fed via a line 7 to the tar separation or to the tar collecting vessel. The coke oven crude gas is fed to a device 4 for separating out the naphthalene in which the naphthalene is separated out by direct cooling with water and is separated from the water. The naphthalene is fed via a line 8 to a separating device which has not been shown and in which the naphthalene is separated from residual water adhering to it. This residual water can be supplied as cooling water. The cooling water is fed in a circulating path through a line 11, a cooler 12 and a line 13. Surplus water is fed via a line 9 to the crude gas condenser 2. The coke oven crude gas is fed to a cleaning unit 5 where it is freed from hydrogen sulfide, ammonia and optionally form benzene before it is supplied to a coke oven gas consumer 6.

Figure 2:
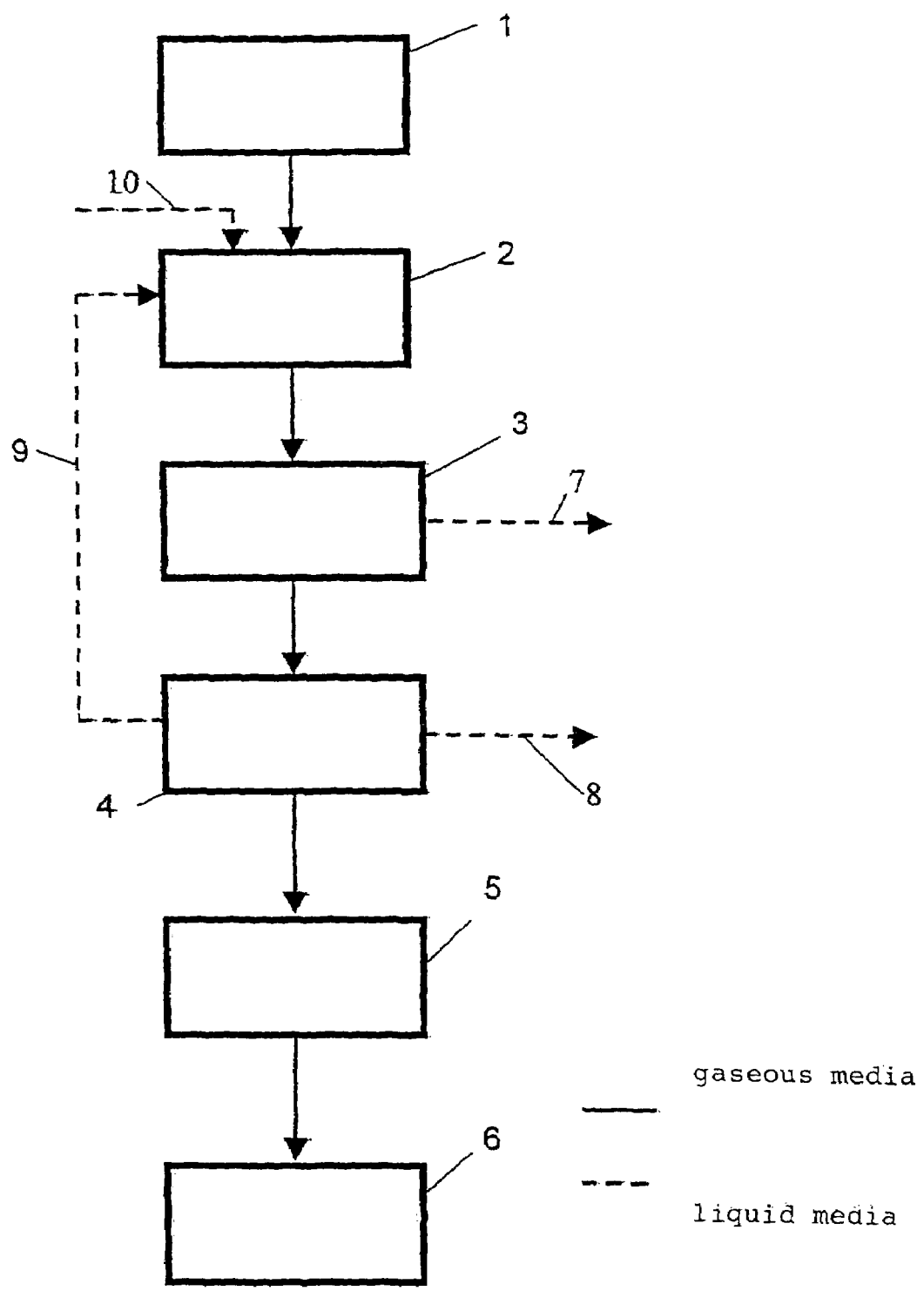
FIG. 2 is a schematic illustration of the method for recovering naphthalene from coke oven crude gas with indirect cooling.

In FIG. 2, the process variant with in direct cooling for the for the recovery of naphthalene has been illustrated. The reference characters have the same significance as in FIG. 1. The coke oven crude gas is fed from the electrostatic filter 3 into a device 4 for crystallizing out the naphthalene and in which the naphthalene is deposited on the cooling surface while the water vapor which is condensed out is carried away via the line 9 to the crude gas condenser 2. The naphthalene crystallized out on the cooling surfaces is drawn off as liquid naphthalene from the device 4 upon heating of the cooling surfaces and is transported through a heated duct 8 to a shipment facility (not shown).

Figure 3:
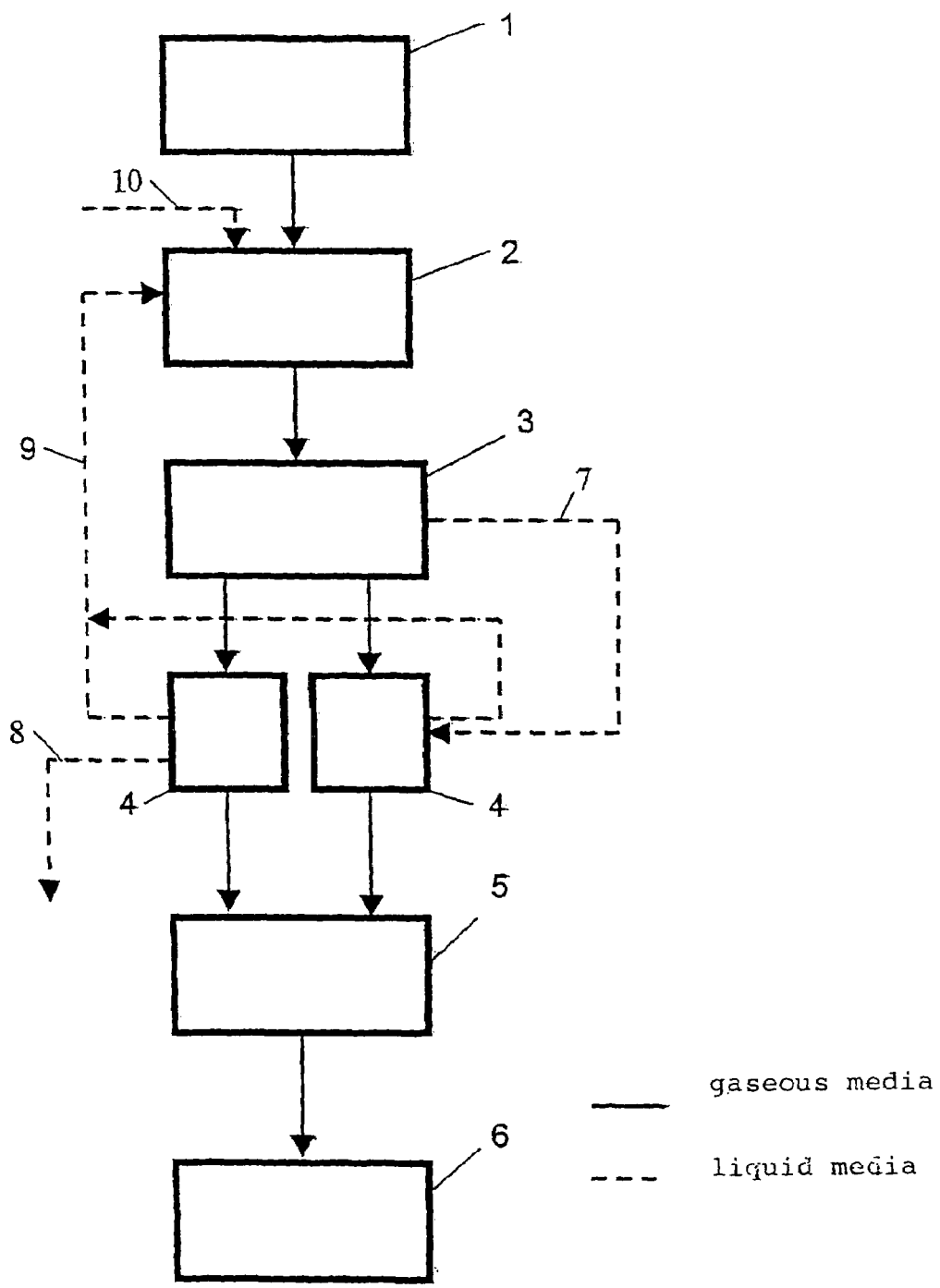
FIG. 3 is a schematic illustration of the method variant according to which part from the recovery of naphthalene a conventional crude gas filling can be carried out.

In FIG. 3, a process scheme has been shown in which two precoolers 4 and 4' are used for crystallizing out the naphthalene. The device 4 is used for naphthalene recovery, that is obtaining the pure naphthalene as transported by the line 8 to the shipment facility. The device 4' is used in precooler operation. The low-naphthalene tar is used in this case for flushing the precooler 4' to prevent blockage by naphthalene. The remaining reference characters have the same significance as in FIG. 1.

| Reference Characters | |
|---|---|
| 1. | Coke Oven |
| 2. | Condenser |
| 3. | Electrostatic Filter |
| 4. | Apparatus for cooling |
| 5. | Coke Oven Gas Cleaning |
| 6. | Coke Oven consumer |
| 7. | Line [Conduit] (Tar) |
| 8. | Line [Conduit] (Naphthalene) |
| 9. | Line [Conduit] (Condensate) |
| 10. | Line [Conduit] (Trickling Water) |
| 11. | Line [Conduit] (Cooling Water) |
| 12. | Cooler |
| 13. | Line [Conduit] (Cooling Water Recycle) |

The invention claimed is:

1. A method of recovering pure naphthalene from a hot crude coke oven gas containing naphthalene, tars, and solid impurities, which comprises the steps of:
    (a) directly cooling the hot crude coke oven gas to a temperature of about 80° C. to obtain a cooled crude coke oven gas and a liquid phase containing tar and solid impurities;
    (b) conducting the cooled crude coke oven gas through an electrostatic filter, wherein the electrostatic filter is insulated or heated so that it is operated isothermally, to remove the tar and the solid impurities to obtain a cooled crude coke oven gas with a tar and solid impurities content reduced by 99.99% and containing naphthalene predominantly in the gaseous phase;
    (c) cooling the crude coke oven gas containing naphthalene predominantly in the gaseous phase from a temperature of about 80° C. to a temperature of about 20° C. so that the naphthalene contained in the cooled crude coke oven gas deposits out as pure crystallized naphthalene; and
    (d) directly recovering the pure naphthalene.

2. The method defined in claim 1 wherein according to step (a) the hot crude coke oven gas has a starting temperature of about 800° C.

3. The method defined in claim 1 wherein according to step (c) the cooling of the crude coke oven gas containing naphthalene predominantly in the gaseous phase is a direct cooling.

4. The method defined in claim 1 wherein according to step (c) the cooling of the crude coke oven gas containing naphthalene predominantly in the gaseous phase is an indirect cooling.

5. The method defined in claim 1 wherein according to step (d) the naphthalene is recovered by heating up.

6. The method defined in claim 5 wherein the heating up is direct heating.

7. The method defined in claim 5 wherein the heating up is indirect heating.

8. The method defined in claim 5 wherein the heating up is carried out with already heated naphthalene.

9. The method defined in claim 1 wherein following step (c) the deposited naphthalene is dissolved with a solvent and the solvent is then removed.

10. The method defined in claim 1 wherein according to step (d) the deposited out naphthalene is mechanically recovered.

11. The method defined in claim 1 wherein according to step (d) the deposited out naphthalene is continuously recovered.

12. An apparatus for recovering pure naphthalene from a hot crude coke-oven gas containing naphthalene, tar, and solid particles:
    means for conducting a stream of the hot coke-oven gas along a flow path passing sequentially through a first cooling station, a filter station downstream of the first cooling station, and a second cooling station downstream of the filter station;
    means in the first cooling station for directly cooling the gas stream to a temperature of about 80° C. and thereby precipitating the tar and solid particles from the stream;
    means in the filter station for maintaining isothermal conditions including an electrostatic filter for removing the tar and particles from the stream;
    a collection surface in the second cooling station for collecting pure crystallized naphthalene; and
    means in the second cooling station for cooling the gas stream to about 20° C. and thereby precipitating the naphthalene from the stream onto the collection surface.

13. The apparatus defined in claim 12 wherein the second cooling station includes heating rods.

14. The apparatus defined in claim 12 wherein the second cooling station is equipped with controllable valves in a segmentwise manner.

15. The apparatus defined in claim 12 wherein the collection surface for recovering the pure naphthalene includes a cooling surface provided with at least one shaver.

16. The apparatus defined in claim 12 wherein the collection surface for recovering the pure naphthalene includes a cooled drum equipped with at least one shaver.

17. The apparatus defined in claim 12 wherein the collection surface for recovering the pure crystallized naphthalene includes a cooled disk equipped with at least one shaver.

18. The apparatus defined in claim 12 wherein the collection surface for recovering the pure crystallized naphthalene includes a tube provided with a tube cooler.

19. The apparatus defined in claim 12 wherein the collection surface for recovering the pure crystallized naphthalene includes at least one vibration generator provided with a cooling surface.

* * * * *